(12) United States Patent
Nishibayashi et al.

(10) Patent No.: US 7,357,776 B2
(45) Date of Patent: Apr. 15, 2008

(54) ACTIVITY-INDUCED ENERGY EXPENDITURE ESTIMATING INSTRUMENT

(75) Inventors: Kenji Nishibayashi, Tokyo (JP); Takashi Shiokawa, Tokyo (JP)

(73) Assignee: Tanita Corporation, Tokyo (JP)

( * ) Notice: Subject to any disclaimer, the term of this patent is extended or adjusted under 35 U.S.C. 154(b) by 0 days.

(21) Appl. No.: 11/723,582

(22) Filed: Mar. 21, 2007

(65) Prior Publication Data

US 2007/0238938 A1 Oct. 11, 2007

(30) Foreign Application Priority Data

Mar. 23, 2006 (JP) .............................. 2006-081403

(51) Int. Cl.
*A61B 5/103* (2006.01)
*A61B 5/117* (2006.01)

(52) U.S. Cl. ..................................... 600/595
(58) Field of Classification Search ................. 600/595
See application file for complete search history.

(56) References Cited

U.S. PATENT DOCUMENTS

| 4,757,453 A * | 7/1988 | Nasiff .......................... 600/595 |
| 7,008,350 B1 * | 3/2006 | Yamazaki et al. .......... 600/300 |
| 7,125,386 B2 * | 10/2006 | Kasahara ..................... 600/595 |
| 2003/0143287 A1 * | 7/2003 | Bell ............................. 424/655 |
| 2005/0043647 A1 * | 2/2005 | Kodama ...................... 600/551 |

FOREIGN PATENT DOCUMENTS

| JP | 11-206743 A | 8/1998 |
| JP | 2005-58614 A | 3/2005 |

* cited by examiner

*Primary Examiner*—Max F. Hindenburg
*Assistant Examiner*—Emily M Lloyd
(74) *Attorney, Agent, or Firm*—McDermott Will & Emery LLP

(57) ABSTRACT

An activity-induced energy expenditure estimating instrument is provided which is capable of estimating an activity-induced energy expenditure with ease and high accuracy. The activity-induced energy expenditure estimating instrument comprises: body activity information measuring means, body specifying information acquiring means, body composition information acquiring means, and activity-induced energy expenditure computing means, wherein the body activity information measuring means measures body activity information, the body specifying information acquiring means acquires body specifying information, the body composition information acquiring means acquires body composition information, and the activity-induced energy expenditure computing means calculates an activity-induced energy expenditure corresponding to these body activity information, body specifying information and body composition information, by use of correlation data representing correlations between the body activity information, body specifying information and body composition information and an activity-induced energy expenditure.

7 Claims, 5 Drawing Sheets

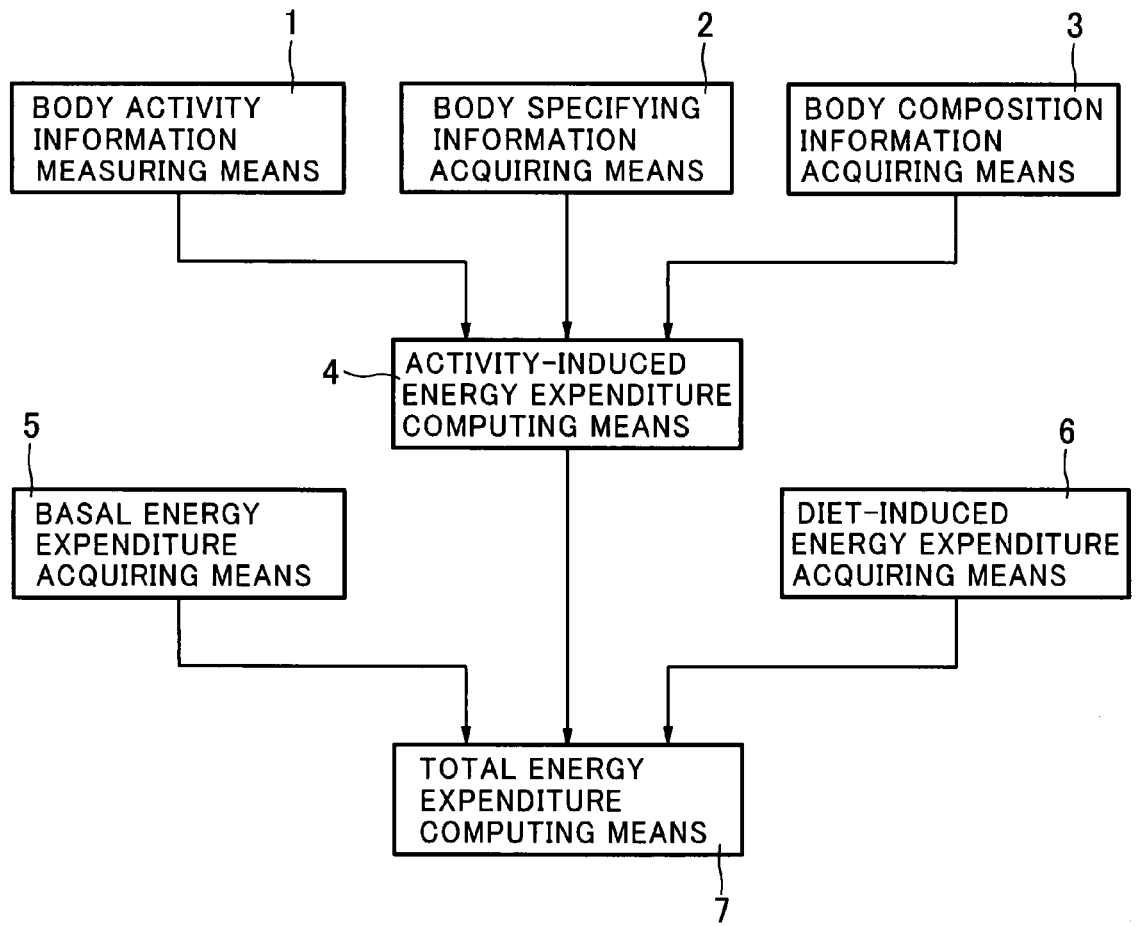
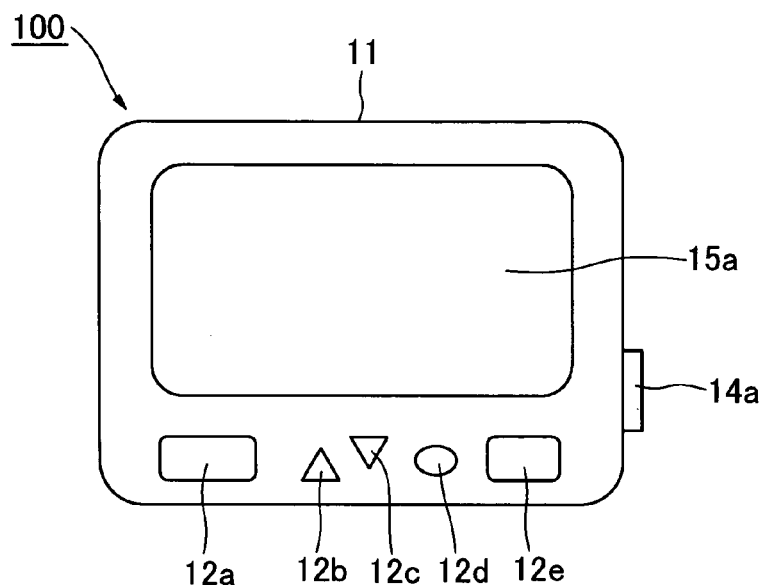

ACTIVITY-INDUCED ENERGY EXPENDITURE ESTIMATING INSTRUMENT

BACKGROUND OF THE INVENTION (i) Field of the Invention

This invention relates to an activity-induced energy expenditure estimating instrument which estimates an activity-induced energy expenditure based on body activity information.

(ii) Description of the Related Art

A variety of instruments which are capable of determining an energy expenditure (calorie expenditure) based on body activity information have been disclosed and provided as tools for obesity prevention or health management.

As for the energy expenditure, most of these various instruments are capable of determining an energy expenditure (generally referred to as "activity-induced energy expenditure", "activity-induced calorie expenditure" or the like) that has been receiving particular attention because its value greatly changes according to the activity of a body.

Illustrative examples of such instruments include instruments capable of determining a basal metabolic rate, an activity-induced energy expenditure and a total energy expenditure in each menstruation-related physical change period of females, such as a female body expenditure information meter described in Patent Literature 1, and instruments capable of determining calorie expenditures in various directions, such as an activity-induced calorie expenditure meter described in Patent Literature 2.

The female body expenditure information meter described in Patent Literature 1 uses formulae (15) and (16) described in this literature to determine an activity-induced energy expenditure that serves as a base in determining an activity-induced energy expenditure in each menstruation-related physical change period of females by use of formulae (16), (17) and (46) to (50) described in this literature. That is, the instrument described in Patent Literature 1 determines an activity-induced energy expenditure by use of age, sex and a body weight and the number of steps as estimation elements. Further, the activity-induced calorie expenditure meter described in Patent Literature 2 determines a calorie expenditure in each direction by use of formulae (3) to (8) described in this literature. That is, the instrument described in Patent Literature 2 determines activity-induced calorie expenditures by use of a body weight and velocity as estimation elements.

As described above, the conventional instruments determine energy expended by activity by use of body specifying information (indicator of an attribute, characteristic or form (size of the outer shape of a body (whole or partial) with respect to a whole body)) such as age, sex and a body weight and body activity information (indicator of magnitude based on activity of a body) such as the number of steps and velocity or acceleration.

Patent Literature 1
  Japanese Patent Laid-Open Publication No. 2005-58614

Patent Literature 2
  Japanese Patent Laid-Open Publication No. 1999-206743

In recent years, more accurate information on energy expended by activity which has been receiving particular attention has been demanded in the market.

In view of the characteristics of the above prior art, an object of the present invention is to provide an activity-induced energy expenditure estimating instrument capable of estimating an activity-induced energy expenditure with ease and higher accuracy than the above prior art.

SUMMARY OF THE INVENTION

According to studies made by the present inventor, the following has been revealed. "In a body, glycogen (glucose) exists primarily in muscles, triglyceride exists primarily in fat cells, free fatty acid exists primarily in blood, and expenditure of energy by activity occurs as a result of expenditure of glycogen, triglyceride, free fatty acid or the like. Further, glycogen, triglyceride and free fatty acid differ in the degree of expenditure by activity. Further, body composition information such as a muscle amount or a fat mass varies from individual to individual, and since glycogen, triglyceride and free fatty acid exist as described above, their proportions which are stored as body composition information such as a muscle amount and a fat mass also vary from individual to individual. Further, since the fat mass becomes a load as weight at the time of activity, it increases an activity-induced energy expenditure per unit muscle amount. From these points, body composition information such as a muscle amount (fat free mass) and a fat mass greatly influences a change in activity-induced energy expenditure."

Thus, the present inventor has invented the following activity-induced energy expenditure estimating instrument of the present invention to achieve the above object.

According to one aspect, the activity-induced energy expenditure estimating instrument of the present invention comprises:
body activity information measuring means,
body specifying information acquiring means,
body composition information acquiring means, and
activity-induced energy expenditure computing means,
wherein
the body activity information measuring means measures body activity information,
the body specifying information acquiring means acquires body specifying information,
the body composition information acquiring means acquires body composition information, and
the activity-induced energy expenditure computing means stores correlation data representing correlations between the body activity information, body specifying information, body composition information, and an activity-induced energy expenditure and calculates an activity-induced energy expenditure corresponding to the body activity information measured by the body activity information measuring means, the body specifying information acquired by the body specifying information acquiring means and the body composition information acquired by the body composition information acquiring means, by use of the stored correlation data.

Further, according to one form of this aspect, the body activity information is acceleration, the body specifying information is a body weight, age and sex, and the body composition information is at least one selected from the group consisting of a fat free mass, a muscle amount, a fat mass, total body water and a body cell mass.

Further, according to another form of this aspect, the correlation data is represented by a formula: $AEE = a_1 + b_1 \times X \times W + c_1 \times FFM + d_1 \times A + f_1 \times S$ wherein X represents acceleration, W represents a body weight, A represents age, S represents sex, FFM represents a fat free mass, $a_1$, $b_1$, $c_1$, $d_1$ and $f_1$ represent constants, and AEE represents an activity-induced energy expenditure.

Further, according to still another form of this aspect, the correlation data is represented by a formula: $AEE = a_2 + b_2 \times X \times W + c_2 \times FFM + d_2 \times FM + e_2 \times A + f_2 \times S$ wherein X represents acceleration, W represents a body weight, A represents age, S represents sex, FFM represents a fat free mass, FM represents a fat mass, $a_2$, $b_2$, $c_2$, $d_2$, $e_2$ and $f_2$ represent constants, and AEE represents an activity-induced energy expenditure.

Further, according to still another form of this aspect, the body activity information is acceleration, the body specifying information is a body weight, age, sex or a body height, the body composition information is at least one selected from the group consisting of a fat free mass, a muscle amount, a fat mass, total body water and a body cell mass.

Further, according to still another form of this aspect, the correlation data is represented by a formula: $AEE = a_3 + b_3 \times X \times W + c_3 \times FFM/H^2 + d_3 \times A + f_3 \times S$ wherein X represents acceleration, W represents a body weight, A represents age, S represents sex, H represents a body height, FFM represents a fat free mass, $a_3$, $b_3$, $c_3$, $d_3$ and $f_3$ represent constants, and AEE represents an activity-induced energy expenditure.

Further, according to still another form of this aspect, the correlation data is represented by a formula: $AEE = a_4 + b_4 \times X \times W + c_4 \times FFM/H^2 + d_4 \times FM + e_4 \times A + f_4 \times S$ wherein X represents acceleration, W represents a body weight, A represents age, S represents sex, H represents a body height, FFM represents a fat free mass, FM represents a fat mass, $a_4$, $b_4$, $c_4$, $d_4$, $e_4$ and $f_4$ represent constants, and AEE represents an activity-induced energy expenditure.

Further, according to still another form of this aspect, the body composition information acquiring means acquires the body composition information from each body part, and the activity-induced energy expenditure computing means stores correlation data representing correlations between the body activity information, body specifying information and body composition information of each body part and an activity-induced energy expenditure, and calculates an activity-induced energy expenditure corresponding to the body activity information measured by the body activity information measuring means, the body specifying information acquired by the body specifying information acquiring means and the body composition information of each body part which has been acquired by the body composition information acquiring means.

Further, according to still another form of this aspect, the body activity information is acceleration, the body specifying information is a body weight, age and sex, and the body composition information of each body part is at least one selected from the group consisting of a fat free mass of each body part, a muscle amount of each body part, a fat mass of each body part, total body water of each body part and a body cell mass of each body part.

Further, according to still another form of this aspect, the correlation data is represented by a formula: $AEE = (\alpha 1_1 + \beta 1_1 \times X \times W + \gamma 1_1 \times FFM_1 + \epsilon 1_1 \times A + \zeta 1_1 \times S) + (\alpha 1_2 + \beta 1_2 \times X \times W + \gamma 1_2 \times FFM_2 + \epsilon 1_2 \times A + \zeta 1_2 \times S) + \ldots + (\alpha 1_n + \beta 1_n \times X \times W + \gamma 1_n \times FFM_n + \epsilon 1_n \times A + \zeta 1_n \times S)$ wherein X represents acceleration, W represents a body weight, A represents age, S represents sex, $FFM_1$, $FFM_2$, ... $FFM_n$ (n represents the number of body parts) represent fat free masses of body parts, $\alpha 1_1$, $\alpha 1_2$, ... $\alpha 1_n$, $\beta 1_1$, $\beta 1_2$, ... $\beta 1_n$, $\gamma 1_1$, $\gamma 1_2$, ... $\gamma 1_n$, $\epsilon 1_1$, $\epsilon 1_2$, ... $\epsilon 1_n$, $\zeta 1_1$, $\zeta 1_2$, ... $\zeta 1_n$ (n represents the number of body parts) represent constants, and AEE represents an activity-induced energy expenditure.

Further, according to still another form of this aspect, the correlation data is represented by a formula: $AEE = (\alpha 2_1 + \beta 2_1 \times X \times W + \gamma 2_1 \times FFM_1 + \delta 2_1 \times FM_1 + \epsilon 2_1 \times A + \zeta 2_1 \times S) + (\alpha 2_2 + \beta 2_2 \times X \times W + \gamma 2_2 \times FFM_2 + \delta 2_2 \times FM_2 + \epsilon 2_2 \times A + \zeta 2_2 \times S) + \ldots + (\alpha 2_n + \beta 2_n \times X \times W + \gamma 2_n \times FFM_n + \delta 2_n \times FM_n + \epsilon 2_n \times A + \zeta 2_n \times S)$ wherein X represents acceleration, W represents a body weight, A represents age, S represents sex, $FFM_1$, $FFM_2$, ... $FFM_n$ (n represents the number of body parts) represent fat free masses of body parts, $FM_1$, $FM_2$, ... $FM_n$ (n represents the number of body parts) represent fat masses of body parts, $\alpha 2_1$, $\alpha 2_2$, ... $\alpha 2_n$, $\beta 2_1$, $\beta 2_2$, ... $\beta 2_n$, $\gamma 2_1$, $\gamma 2_2$, ... $\gamma 2_n$, $\delta 2_1$, $\delta 2_2$, ... $\delta 2_n$, $\epsilon 2_1$, $\epsilon 2_2$, ... $\epsilon 2_n$, $\zeta 2_1$, $\zeta 2_2$, ... $\zeta 2_n$ (n represents the number of body parts) represent constants, and AEE represents an activity-induced energy expenditure.

Further, according to still another form of this aspect, the activity-induced energy expenditure estimating instrument of the present invention further comprises:
basal energy expenditure acquiring means,
diet-induced energy expenditure acquiring means, and
total energy expenditure computing means,
wherein
the basal energy expenditure acquiring means acquires a basal metabolic rate or a rest metabolic rate,
the diet-induced energy expenditure acquiring means acquires a diet-induced energy expenditure, and
the total energy expenditure computing means calculates a total energy expenditure by totalizing the activity-induced energy expenditure acquired by the activity-induced energy expenditure computing means, the basal metabolic rate or rest metabolic rate acquired by the basal energy expenditure acquiring means and the diet-induced energy expenditure acquired by the diet-induced energy expenditure acquiring means.

The activity-induced energy expenditure estimating instrument of the present invention comprises:
body activity information measuring means,
body specifying information acquiring means,
body composition information acquiring means, and
activity-induced energy expenditure computing means,
wherein
the body activity information measuring means measures body activity information,
the body specifying information acquiring means acquires body specifying information,
the body composition information acquiring means acquires body composition information, and
the activity-induced energy expenditure computing means calculates an activity-induced energy expenditure corresponding to these body activity information, body specifying information and body composition information, by use of correlation data representing correlations between the body activity information, body specifying information and body composition information and an activity-induced energy expenditure. That is, since the present instrument takes into consideration body composition information which greatly influences a change in activity-induced energy expenditure to estimate the activity-induced energy expenditure, it can estimate the activity-induced energy expenditure with ease and high accuracy.

Further, in particular, since the body activity information is acceleration, the body specifying information is a body weight, age and sex, and the body composition information is at least one selected from the group consisting of a fat free mass, a muscle amount, a fat mass, total body water and a body cell mass, an activity-induced energy expenditure can be estimated securely and with ease and high accuracy.

Further, in particular, since the correlation data is represented by a formula: $AEE = a_1 + b_1 \times X \times W + c_1 \times FFM + d_1 \times A + f_1 \times S$ wherein X represents acceleration, W represents a body weight, A represents age, S represents sex, FFM represents a fat free mass, $a_1$, $b_1$, $c_1$, $d_1$ and $f_1$ represent constants, and AEE represents an activity-induced energy expenditure, an activity-induced energy expenditure can be estimated securely and with ease and higher accuracy.

Further, in particular, since the correlation data is represented by a formula: $AEE=a_2+b_2 \times X \times W+c_2 \times FFM+d_2 \times FM+e_2 \times A+f_2 \times S$ wherein X represents acceleration, W represents a body weight, A represents age, S represents sex, FFM represents a fat free mass, FM represents a fat mass, $a_2$, $b_2$, $c_2$, $d_2$, $e_2$ and $f_2$ represent constants, and AEE represents an activity-induced energy expenditure, an activity-induced energy expenditure can be estimated securely and with ease and higher accuracy.

Further, in particular, since the body activity information is acceleration, the body specifying information is a body weight, age, sex or a body height, the body composition information is at least one selected from the group consisting of a fat free mass, a muscle amount, a fat mass, total body water and a body cell mass, an activity-induced energy expenditure can be estimated securely and with ease and high accuracy.

Further, in particular, since the correlation data is represented by a formula: $AEE=a_3+b_3 \times X \times W+c_3 \times FFM/H^2+d_3 \times A+f_3 \times S$ wherein X represents acceleration, W represents a body weight, A represents age, S represents sex, H represents a body height, FFM represents a fat free mass, $a_3$, $b_3$, $c_3$, $d_3$ and $f_3$ represent constants, and AEE represents an activity-induced energy expenditure, an activity-induced energy expenditure can be estimated securely and with ease and higher accuracy.

Further, in particular, since the correlation data is represented by a formula: $AEE=a_4+b_4 \times X \times W+c_4 \times FFM/H^2+d_4 \times FM+e_4 \times A+f_4 \times S$ wherein X represents acceleration, W represents a body weight, A represents age, S represents sex, H represents a body height, FFM represents a fat free mass, FM represents a fat mass, $a_4$, $b_4$, $c_4$, $d_4$, $e_4$ and $f_4$ represent constants, and AEE represents an activity-induced energy expenditure, an activity-induced energy expenditure can be estimated securely and with ease and higher accuracy.

Further, since the body composition information acquiring means acquires the body composition information from each body part and the activity-induced energy expenditure computing means calculates an activity-induced energy expenditure corresponding to the body activity information, body specifying information and body composition information of each body part by use of correlation data representing correlations between the body activity information, body specifying information and body composition information of each body part and an activity-induced energy expenditure, an activity-induced energy expenditure can be estimated securely and with ease and high accuracy.

Further, since the body activity information is acceleration, the body specifying information is a body weight, age and sex, and the body composition information of each body part is at least one selected from the group consisting of a fat free mass of each body part, a muscle amount of each body part, a fat mass of each body part, total body water of each body part and a body cell mass of each body part, an activity-induced energy expenditure can be estimated more securely and with ease and high accuracy.

Further, in particular, since the correlation data is represented by a formula: $AEE=(\alpha 1_1+\beta 1_1 \times X \times W+\gamma 1_1 \times FFM_1+\epsilon 1_1 \times A+\zeta 1_1 \times S)+(\alpha 1_2+\beta 1_2 \times X \times W+\gamma 1_2 \times FFM_2+\epsilon 1_2 \times A+\zeta 1_2 \times S)+\ldots+(\alpha 1_n+\beta 1_n \times X \times W+\gamma 1_n \times FFM_n+\epsilon 1_n \times A+\zeta 1_n \times S)$ wherein X represents acceleration, W represents a body weight, A represents age, S represents sex, $FFM_1$, $FFM_2$, ... $FFM_n$ (n represents the number of body parts) represent fat free masses of body parts, $\alpha 1_1$, $\alpha 1_2$, ... $\alpha 1_n$, $\beta 1_1$, $\beta 1_2$, ... $\beta 1_n$, $\gamma 1_1$, $\gamma 1_2$, ... $\gamma 1_n$, $\epsilon 1_1$, $\epsilon 1_2$, ... $\epsilon 1_n$, $\zeta 1_1$, $\zeta 1_2$, ... $\zeta 1_n$ (n represents the number of body parts) represent constants, and AEE represents an activity-induced energy expenditure, an activity-induced energy expenditure can be estimated more securely and with ease and higher accuracy.

Further, in particular, since the correlation data is represented by a formula: $AEE=(\alpha 2_1+\beta 2_1 \times X \times W+\gamma 2_1 \times FFM_1+\delta 2_1 \times FM_1+\epsilon 2_1 \times A+\zeta 2_1 \times S)+(\alpha 2_2+\beta 2_2 \times X \times W+\gamma 2_2 \times FFM_2+\delta 2_2 \times FM_2+\epsilon 2_2 \times A+\zeta 2_2 \times S)+\ldots+(\alpha 2_n+\beta 2_n \times X \times W+\gamma 2_n \times FFM_n+\delta 2_n \times FM_n+\epsilon 2_n \times A+\zeta 2_n \times S)$ wherein X represents acceleration, W represents a body weight, A represents age, S represents sex, $FFM_1$, $FFM_2$, ... $FFM_n$ (n represents the number of body parts) represent fat free masses of body parts, $FM_1$, $FM_2$, ... $FM_n$ (n represents the number of body parts) represent fat masses of body parts, $\alpha 2_1$, $\alpha 2_2$, ... $\alpha 2_n$, $\beta 2_1$, $\beta 2_2$, ... $\beta 2_n$, $\gamma 2_1$, $\gamma 2_2$, ... $\gamma 2_n$, $\delta 2_1$, $\delta 2_2$, ... $\delta 2_n$, $\epsilon 2_1$, $\epsilon 2_2$, ... $\epsilon 2_n$, $\zeta 2_1$, $\zeta 2_2$, ... $\zeta 2_n$ (n represents the number of body parts) represent constants, and AEE represents an activity-induced energy expenditure, an activity-induced energy expenditure can be estimated more securely and with ease and higher accuracy.

Further, the activity-induced energy expenditure estimating instrument of the present invention also comprises:
basal energy expenditure acquiring means,
diet-induced energy expenditure acquiring means, and
total energy expenditure computing means,
wherein
the basal energy expenditure acquiring means acquires a basal metabolic rate or a rest metabolic rate,
the diet-induced energy expenditure acquiring means acquires a diet-induced energy expenditure, and
the total energy expenditure computing means calculates a total energy expenditure by totalizing these basal metabolic rate or rest metabolic rate, diet-induced energy expenditure and an activity-induced energy expenditure. Thus, the present instrument can also estimate the total energy expenditure associated with an activity-induced energy expenditure with ease and high accuracy.

BRIEF DESCRIPTION OF THE DRAWINGS

FIG. 1 is a block diagram showing the functional constitution of an activity-induced energy expenditure estimating instrument.

FIG. 2 is a front view of the activity-induced energy expenditure estimating instrument.

DETAILED DESCRIPTION OF THE PREFERRED EMBODIMENTS

Figure 3:
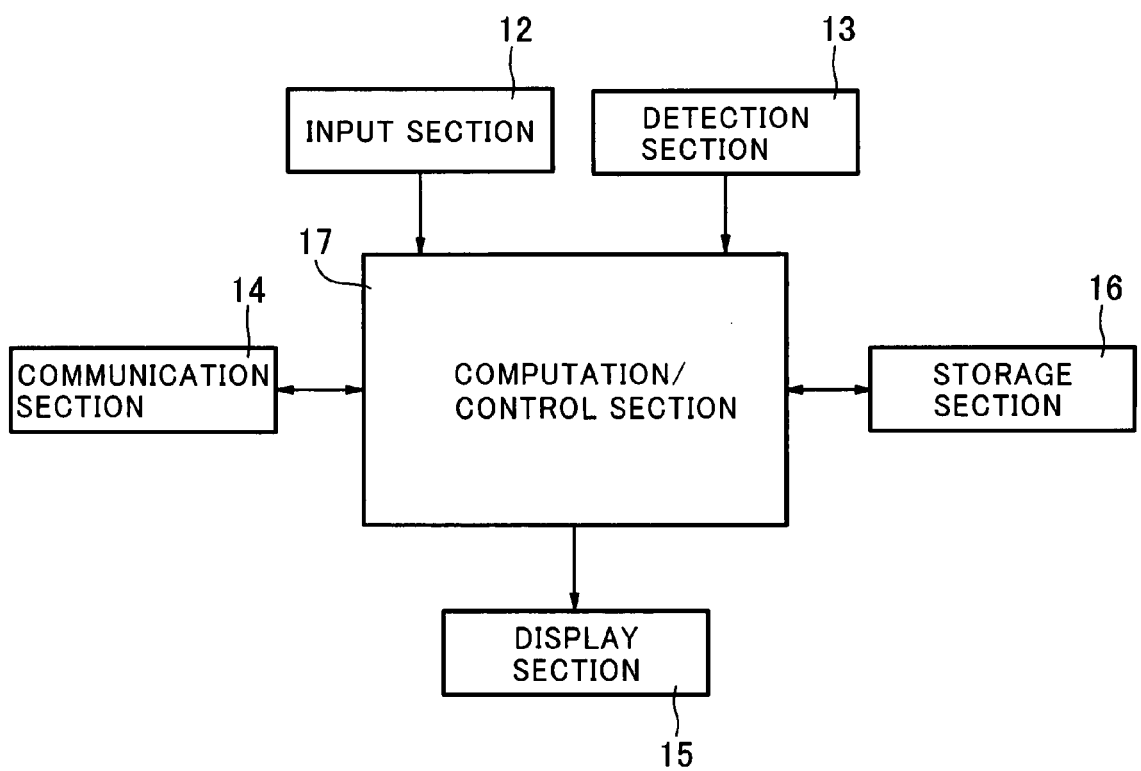
FIG. 3 is a block diagram showing the structural constitution of the activity-induced energy expenditure estimating instrument.

As shown in FIG. 1 which is a block diagram showing functional constitution, an activity-induced energy expenditure estimating instrument of the present invention comprises body activity information measuring means 1, body specifying information acquiring means 2, body composition information acquiring means 3, activity-induced energy expenditure computing means 4, basal energy expenditure acquiring means 5, diet-induced energy expenditure acquiring means 6, and total energy expenditure computing means 7.

The body activity information measuring means 1 measures body activity information (indicator of magnitude based on activity of a body, such as acceleration, velocity and the number of steps).

The body specifying information acquiring means 2 acquires body specifying information (indicator of an attribute, characteristic or form (size of the outer shape of a body (whole or partial)) with respect to a whole body, such as age, sex, a body weight and a body height).

The body composition information acquiring means 3 acquires body composition information (indicator of components in a body, such as a fat free mass (FFM), a muscle amount, a fat mass (FF), total body water (TBW) and a body cell mass (BCM)).

The activity-induced energy expenditure computing means 4 stores correlation data (e.g. AEE=f(M, T, C)) representing correlations between body activity information (M), body specifying information (T) and body composition information (C) and an activity-induced energy expenditure (AEE) and calculates an activity-induced energy expenditure corresponding to body activity information measured by the body activity information measuring means 1, body specifying information acquired by the body specifying information acquiring means 2 and body composition information acquired by the body composition information acquiring means 3, by use of the stored correlation data.

The basal energy expenditure acquiring means 5 acquires a basal energy expenditure (basal metabolic rate (BMR) representing minimum energy required to sustain life or rest metabolic rate (RMR) or resting energy expenditure (REE) representing energy expended in a resting state (state in which one is lying or sitting quietly)).

The diet-induced energy expenditure acquiring means 6 acquires a diet-induced energy expenditure (DEE) representing energy expended upon eating (upon digestion and absorption of food, transfer, metabolism and storage of nutrients).

The total energy expenditure computing means 7 computes a total energy expenditure (TEE) by totalizing the activity-induced energy expenditure acquired by the activity-induced energy expenditure computing means 4, the basal metabolic rate or rest metabolic rate acquired by the basal energy expenditure acquiring means 5 and the diet-induced energy expenditure acquired by the diet-induced energy expenditure acquiring means 6.

According to the thus constituted activity-induced energy expenditure estimating instrument, since it measures body activity information in the body activity information measuring means 1, acquires body specifying information in the body specifying information acquiring means 2, acquires body composition information in the body composition information acquiring means 3, and calculates an activity-induced energy expenditure corresponding to these body activity information, body specifying information and body composition information by use of correlation data representing correlations between the body activity information, body specifying information and body composition information and the activity-induced energy expenditure, it can acquire an activity-induced energy expenditure which takes into consideration body composition information which greatly influences a change in activity-induced energy expenditure. Therefore, the instrument can estimate an activity-induced energy expenditure with ease and high accuracy.

Further, since the instrument acquires a basal metabolic rate or rest metabolic rate in the basal energy expenditure acquiring means 5, acquires a diet-induced energy expenditure in the diet-induced energy expenditure acquiring means 6, and calculates a total energy expenditure by totalizing the acquired basal metabolic rate or rest metabolic rate, the acquired diet-induced energy expenditure and the calculated activity-induced energy expenditure in the total energy expenditure computing means 7, it can also estimate a total energy expenditure associated with an activity-induced energy expenditure with ease and high accuracy.

Hereinafter, an example in the above forms will be described specifically.

EXAMPLE

Firstly, the specific constitution of an activity-induced energy expenditure estimating instrument according to the present invention will be described by primarily using FIG. 2 which is a front view and FIG. 3 which is a block diagram showing structural constitution.

An activity-induced energy expenditure estimating instrument 100 according to the present invention comprises an input section 12, a detection section 13, a communication section 14, a display section 15, a storage section 16 and a computation/control section 17 on an external case 11.

The input section 12 is a section used for inputting or setting various information and comprises, for example, an ON/OFF button 12a, an UP button 12b, a DOWN button 12c, a SETTING button 12d and SWITCHING button 12e on the front side of the external case 11. The ON/OFF button 12a is a switch for activating or deactivating the present instrument 100. The UP button 12b and the DOWN button 12c are switches for specifying information (changing numerical values or selecting information). The SETTING button 12d is a switch for setting information specified by the UP button 12b or the DOWN button 12c. The SWITCHING button 12e is a switch for switching displayed images.

The detection section 13 is a section for detecting acceleration as body activity information and comprises, for example, an acceleration sensor 13a and a detection circuit inside the external case 11.

The communication section 14 is a section for receiving element information (age, sex and a body weight as body specifying information, and a fat free mass and a fat mass as body composition information) required to determine an activity-induced energy expenditure or element information (rest metabolic rate and a diet-induced energy expenditure) required to determine a total energy expenditure and transmitting information of the determined activity-induced energy expenditure or total energy expenditure. The communication section 14 comprises a terminal 14a to connect the instrument 100 to an external device (such as a personal computer) on a side face of the external case 11 and a communication interface circuit inside the external case 11.

The display section 15 is a section for displaying various information set through the input section 12, various information received or transmitted by the communication section 14, and information of activity-induced energy expenditure or total energy expenditure determined by the communication/control section 17. The display section 15 comprises, for example, an LCD 15a on the front side of the external case 11 and a display drive circuit in the external case 11.

The storage section 16 is a section for storing at least (a) correlation data (formula (1): $AEE=a_2+b_2 \times X \times W+c_2 \times FFM+d_2 \times FM+e_2 \times A+f_2 \times S$ wherein X represents acceleration, W represents a body weight, A represents age, S represents sex, FFM represents a fat free mass, FM represents a fat mass, $a_2$, $b_2$, $c_2$, $d_2$, $e_2$ and $f_2$ represent constants, and AEE represents an activity-induced energy expenditure) for determining an activity-induced energy expenditure, (b) a formula (2): $TEE=REE+AEE+DEE$ wherein REE represents a resting energy expenditure, AEE represents an activity-induced energy expenditure, DEE represents a diet-induced energy expenditure, and TEE represents a total energy expenditure, (c) a computation/control program for determining an activity-induced energy expenditure and a total energy expenditure, (d) various information set through the input section 12, (e) information received by the communication section 14, such as age, sex, a body weight, a fat free mass, a fat mass, a rest metabolic rate and a diet-induced energy expenditure, and (f) information of activity-induced energy expenditure and total energy expenditure determined by the computation/control section 17. The storage section 16 comprises, for example, a ROM, RAM or EEPROM in the external case 11.

Figure 4:
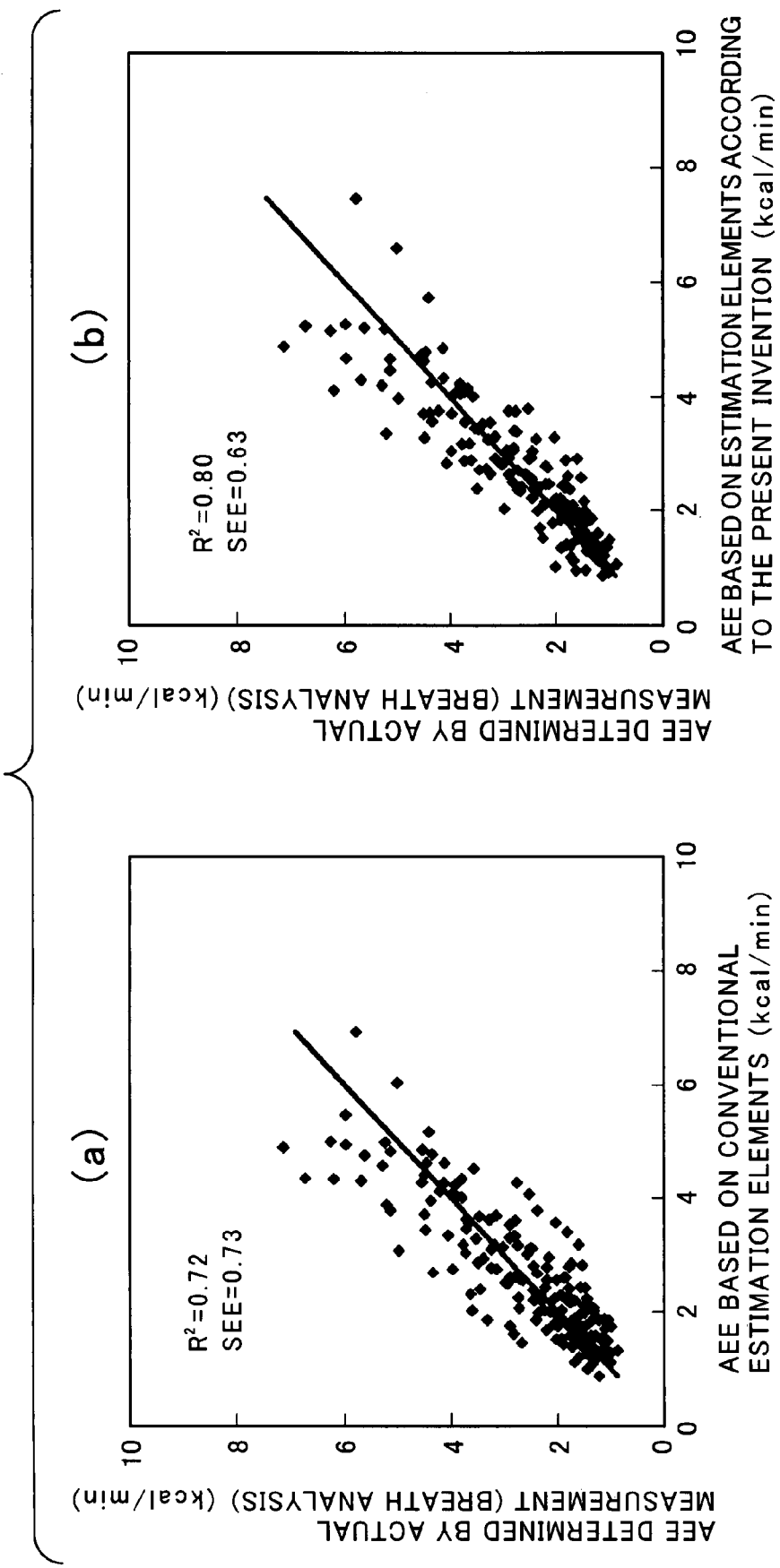
FIG. 4 is graphs showing correlations between an activity-induced energy expenditure determined by actual measurement (breath analysis) and an activity-induced energy expenditure determined by estimation elements, wherein (a) is a graph showing a correlation between an activity-induced energy expenditure determined by breath analysis (AEE determined by actual measurement (breath analysis)) and an activity-induced energy expenditure determined from correlation data including acceleration, age, sex and a body weight as estimation elements (independent variables) (AEE based on conventional estimation elements), and (b) is a graph showing a correlation between an activity-induced energy expenditure determined by breath analysis (AEE determined by actual measurement (breath analysis)) and an activity-induced energy expenditure determined from correlation data including acceleration, age, sex, a body weight, a fat free mass and a fat mass as estimation elements (independent variables) (AEE based on estimation elements according to the present invention).

As for the formula (1) including a fat free mass and a fat mass as estimation elements (independent variables), as is obvious from comparison of the graph shown in FIG. 4(a) which shows a correlation between an activity-induced energy expenditure determined by breath analysis (vertical axis) and an activity-induced energy expenditure determined from correlation data including acceleration, age, sex and a body weight as estimation elements (independent variables) (horizontal axis) with the graph shown in FIG. 4(b) which shows a correlation between an activity-induced energy expenditure determined by breath analysis (vertical axis) and an activity-induced energy expenditure determined from correlation data including acceleration, age, sex, a body weight, a fat free mass and a fat mass as estimation elements (independent variables) (horizontal axis), the graph shown in FIG. 4(b) is more significant than the graph shown in FIG. 4(a) because the graph shown in FIG. 4(b) shows a determination coefficient $R^2$ as a larger value and a standard error of estimate (SEE) as a smaller value.

The computation/control section 17 (A) calculates an activity-induced energy expenditure by substituting age, sex, a body weight, a fat free mass and a fat mass received by the communication section 14 into the formula (1) stored in the storage section 16, (B) calculates a total energy expenditure by substituting the thus calculated activity-induced energy expenditure, a rest metabolic expenditure received by the communication section 14 and a diet-induced energy expenditure received by the communication section 14 into the formula (2) stored in the storage section 16, (C) executes the computation/control program stored in the storage section 16, (D) controls inputting and setting of various information through the input section 12, (E) controls reception of age, sex, a body weight, a fat free mass, a fat mass, a rest metabolic rate and a diet-induced energy expenditure and transmission of information of determined activity-induced energy expenditure and total energy expenditure by the communication section 14, (F) controls detection of acceleration by the detection section 13, and (G) controls display of various information, including information of determined activity-induced energy expenditure and total energy expenditure, by the display section 15. The computation/control section 17 comprises, for example, a CPU in the external case 11.

The detection section 13, the computation/control section 17 and the storage section 16 constitute the body activity information measuring means 1. Further, the communication section 14, the computation/control section 17 and the storage section 16 constitute the body specifying information acquiring means 2, the body composition information acquiring means 3, the basal energy expenditure acquiring means 5 or the diet-induced energy expenditure acquiring means 6. Further, the storage section 16 and the computation/control section 17 constitute the activity-induced energy expenditure computing means 4 or the total energy expenditure computing means 7.

Next, the operation of the activity-induced energy expenditure estimating instrument according to the present invention will be described by primarily using a flowchart shown in FIG. 5.

Figure 5:
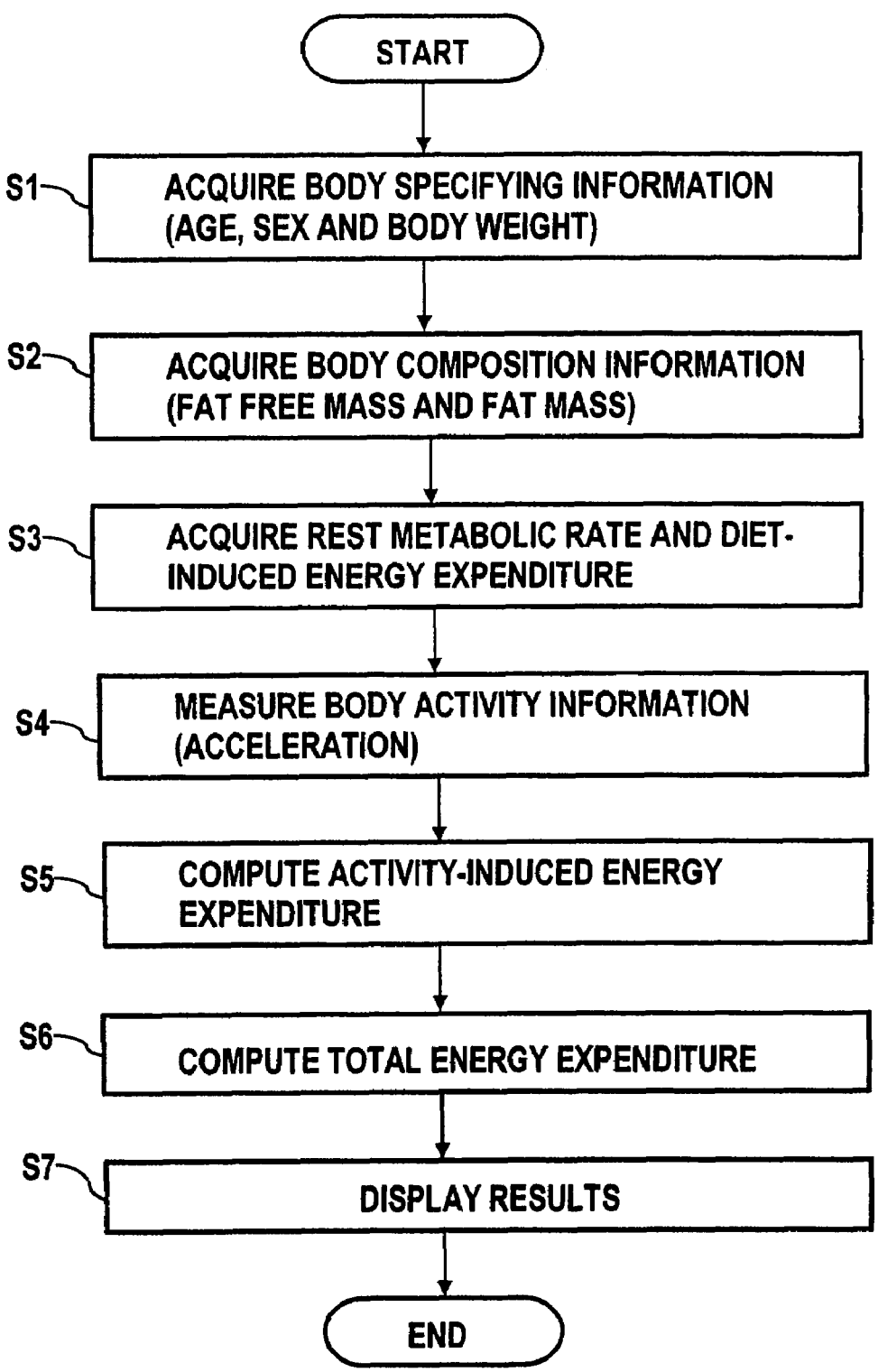
FIG. 5 is a flowchart showing a flow of operations of the activity-induced energy expenditure estimating instrument.

According to the flowchart of FIG. 5, the present instrument is activated at the press of the ON/OFF button 12a. Then, when age, sex and a body weight are output from an external device with the connection terminal 14a and the external device connected to each other directly or by a cord, the present instrument receives the age, sex and body weight output from the external device in the communication section 14 and stores the received age, sex and body weight in the storage section 16 (STEP S1).

Then, when a fat free mass and a fat mass are output from the external device, the present instrument receives the fat free mass and fat mass output from the external device in the communication section 14 and stores the received fat free mass and fat mass in the storage section 16 (STEP S2).

Then, when a rest metabolic rate and a diet-induced energy expenditure are output from the external device, the present instrument receives the rest metabolic rate and diet-induced energy expenditure output from the external device in the communication section 14 and stores the received rest metabolic rate and diet-induced energy expenditure in the storage section 16 (STEP S3).

Figure 6:
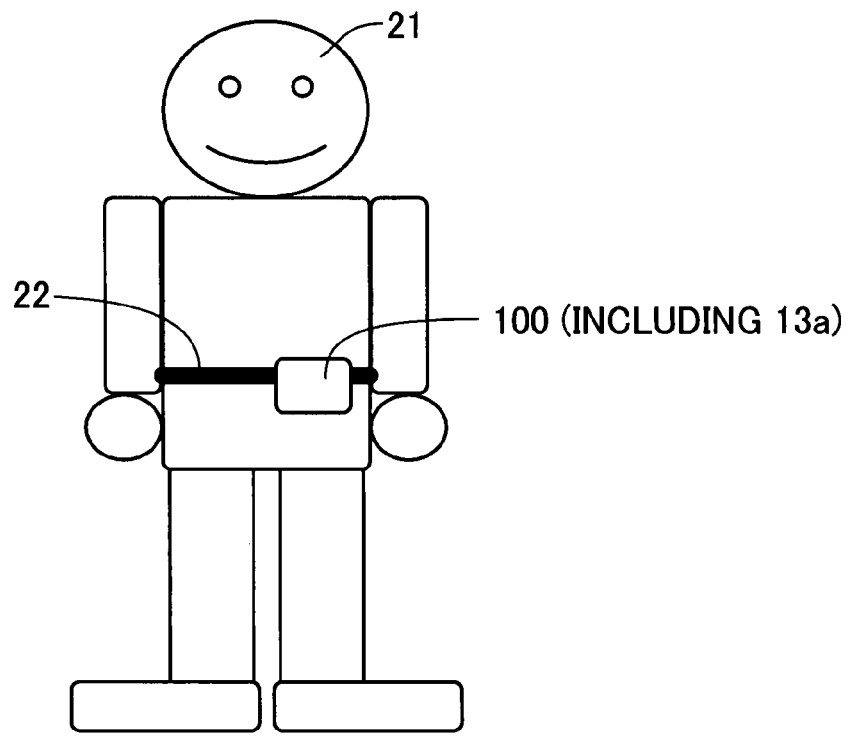
FIG. 6 is a diagram showing an example of how a subject wears the activity-induced energy expenditure estimating instrument (using a single acceleration sensor).

Then, when the present instrument 100 is attached to a belt 22 around the waist of a subject 21 as shown in FIG. 6, the instrument detects acceleration based on body activity of the subject 21 in the detection section 13 and stores the detected acceleration in the storage section 16 (STEP S4).

Then, in the computation/control section 17, the present instrument computes an activity-induced energy expenditure by substituting the age, sex, body weight, fat free mass and fat mass stored in the storage section 16 into the formula (1) stored in advance in the storage section 16 (STEP S5).

Then, in the computation/control section 17, the present instrument computes a total energy expenditure by substituting the computed activity-induced energy expenditure and the rest metabolic expenditure and diet-induced energy expenditure stored in the storage section 16 into the formula (2) stored in advance in the storage section 16 (STEP S6).

Then, the present instrument stores the activity-induced energy expenditure and total energy expenditure computed by the computation/control section 17 in the storage section 16 and displays the activity-induced energy expenditure and total energy expenditure computed by the computation/control section 17 in the display section 15 (STEP S7), thereby ending a series of operations.

Although the activity-induced energy expenditure estimating instrument 100 in the above example measures acceleration as body activity information, it may measure velocity or the number of steps in place of the acceleration. Further, although the instrument 100 acquires a fat free mass and a fat mass as body composition information, it is sufficient to acquire at least one selected from the group consisting of a fat free mass, a fat mass, a muscle amount, total body water and a body cell mass. In particular, since the muscle amount is nearly equal to the fat free mass, it is as significant an estimation element as estimation elements used to generate the graph shown in FIG. 4b.

Further, although the activity-induced energy expenditure estimating instrument in the above example uses a rest metabolic rate, it may use a basal metabolic rate in place of the rest metabolic rate.

Further, although the activity-induced energy expenditure estimating instrument in the above example acquires body specifying information (age, sex and body weight), body composition information (fat free mass and fat mass), a rest metabolic rate and a diet-induced energy expenditure by receiving them in the communication section 14, it may acquire the body specifying information (age, sex and body weight), body composition information (fat free mass and fat mass), rest metabolic rate and diet-induced energy expenditure by inputting and setting them through the input section 12. In that case, the above information is specified by the UP button 12b and the DOWN button 12c, and the specified information is set by the SETTING button 12d.

Further, although the activity-induced energy expenditure estimating instrument in the above example acquires a fat free mass and a fat mass as body composition information and determines an activity-induced energy expenditure by use of the formula (1), it may acquire only a fat free mass as body composition information and determine an activity-induced energy expenditure by use of a formula (3): $AEE = a_1 + b_1 \times X \times W + c_1 \times FFM + d_1 \times A + f_1 \times S$ wherein X represents acceleration, W represents a body weight, A represents age, S represents sex, FFM represents a fat free mass, $a_1, b_1, c_1, d_1,$ and $f_1$ represent constants and AEE represents an activity-induced energy expenditure.

Further, although the activity-induced energy expenditure estimating instrument in the above example acquires age, sex and a body weight as body specifying information in the communication section 14 and determines an activity-induced energy expenditure by use of the formula (1) stored in the storage section 16 in the computation/control section, the instrument may store a formula (6): $AEE = a_3 + b_3 \times X \times W + c_3 \times FFM/H^2 + d_3 \times A + f_3 \times S$ wherein X represents acceleration, W represents a body weight, A represents age, S represents sex, H represents a body height, FFM represents a fat free mass, $a_3, b_3, c_3, d_3$ and $f_3$ represent constants and AEE represents an activity-induced energy expenditure in the storage section and determine an activity-induced energy expenditure by use of the formula (6) stored in the storage section in the computation/control section or may store a formula (7): $AEE = a_4 + b_4 \times X \times W + c_4 \times FFM/H^2 + d_4 \times FM + e_4 \times A + f_4 \times S$ wherein X represents acceleration, W represents a body weight, A represents age, S represents sex, H represents a body height, FFM represents a fat free mass, FM represents a fat mass, $a_4, b_4, c_4, d_4, e_4$ and $f_4$ represent constants and AEE represents an activity-induced energy expenditure in the storage section and determine an activity-induced energy expenditure by use of the formula (7) stored in the storage section in the computation/control section. At least the same estimation effect as that when the formula (1) was used can be obtained.

Figure 7:
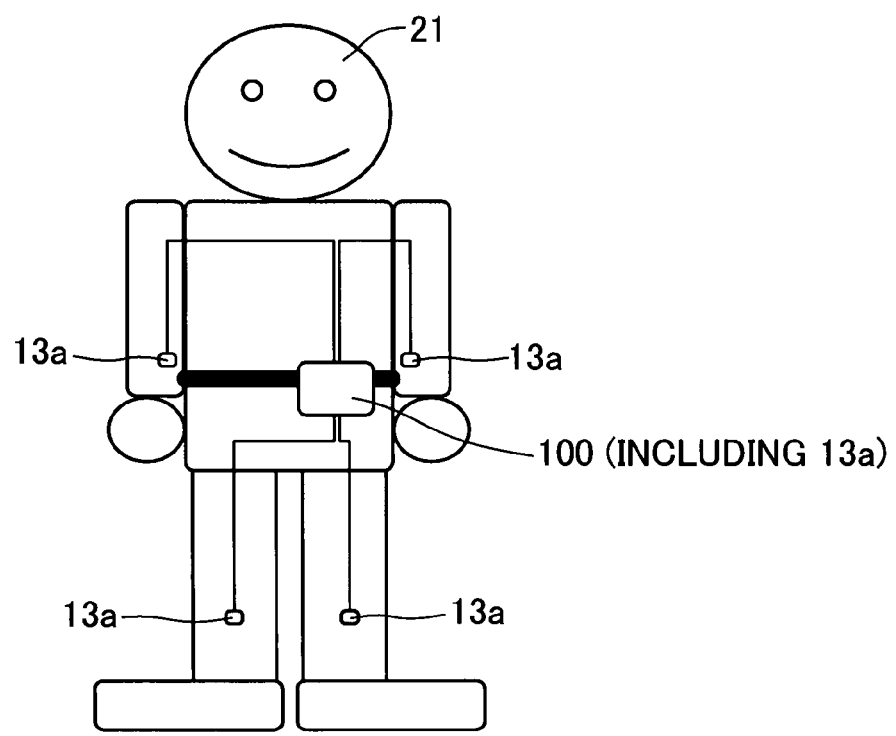
FIG. 7 is a diagram showing an example of how a subject wears the activity-induced energy expenditure estimating instrument (using multiple acceleration sensors).

Further, although the activity-induced energy expenditure estimating instrument in the above example places the detection section 13 (acceleration sensor) only on the belt 22 around the waist of the subject 21 to measure body activity information (acceleration), acquires body composition information (fat free mass and fat mass) of a whole body, and determines an activity-induced energy expenditure by use of the formula (1), the instrument may place the detection section (multiple acceleration sensors) on each body part of the subject, acquire body composition information of each body part of the subject (fat free mass of each body part and fat mass of each body part) and determine an activity-induced energy expenditure by use of a formula (4): $AEE = (\alpha 2_1 + \beta 2_1 \times X \times W + \gamma 2_1 \times FFM_1 + \delta 2_1 \times FM_1 + \epsilon 2_1 \times A + \zeta 2_1 \times S) + (\alpha 2_2 + \beta 2_2 \times X \times W + \gamma 2_2 \times FFM_2 + \delta 2_2 \times FM_2 + \epsilon 2_2 \times A + \zeta 2_2 \times S) + \ldots + (\alpha 2_n + \beta 2_n \times X \times W + \gamma 2_n \times FFM_n + \delta 2_n \times FM_n + \epsilon 2_n \times A + \zeta 2_n \times S)$ wherein X represents acceleration, W represents a body weight, A represents age, S represents sex, $FFM_1, FFM_2, \ldots FFM_n$ (n represents the number of body parts) represent fat free masses of body parts, $FM_1, FM_2, \ldots FM_n$ (n represents the number of body parts) represent fat masses of body parts, $\alpha 2_1, \alpha 2_2, \ldots \alpha 2_n, \beta 2_1, \beta 2_2, \ldots \beta 2_n, \gamma 2_1, \gamma 2_2, \ldots \gamma 2_n, \delta 2_1, \delta 2_2, \ldots \delta 2_n, \epsilon 2_1, \epsilon 2_2, \ldots \epsilon 2_n, \zeta 2_1, \zeta 2_2, \ldots \zeta 2_n$ (n represents the number of body parts) represent constants and AEE represents an activity-induced energy expenditure. For example, as shown in FIG. 7, the instrument may place the detection section (five acceleration sensors 13a) on body parts (for example, trunk, right upper extremity, left upper extremity, right lower extremity, left lower extremity) of the subject 21, acquire body composition information of the body parts of the subject (fat free mass $FFM_1$ of the trunk, fat free mass $FFM_2$ of the right upper extremity, fat free mass $FFM_3$ of the left upper extremity, fat free mass $FFM_4$ of the right lower extremity, fat free mass $FMM_5$ of the left lower extremity, fat mass $FM_1$ of the trunk, fat mass $FM_2$ of the right upper extremity, fat mass $FM_3$ of the left upper extremity, fat mass $FM_4$ of the right lower extremity, fat mass $FM_5$ of the left lower extremity) and determine an activity-induced energy expenditure by substituting the acquired information into a formula: $AEE = (\alpha_1 + \beta_1 \times X \times W + \gamma_1 \times FFM_1 + \delta_1 \times FM_1 + \epsilon_1 \times A + \zeta_1 \times S) + (\alpha_2 + \beta_2 \times X \times W + \gamma_2 \times FFM_2 + \delta_2 \times FM_2 + \epsilon_2 \times A + \zeta_2 \times S) + (\alpha_3 + \beta_3 \times X \times W + \gamma_3 \times FFM_3 + \delta_3 \times FM_3 + \epsilon_3 \times A + \zeta_3 \times S) + (\alpha_4 + \beta_4 \times X \times W + \gamma_4 \times FFM_4 + \delta_4 \times FM_4 + \epsilon_4 \times A + \zeta_4 \times S) + (\alpha_5 + \beta_5 \times X \times W + \gamma_5 \times FFM_5 + \delta_5 \times FM_5 + \epsilon_5 \times A + \zeta_5 \times S)$.

Alternatively, the instrument may place the detection section (multiple acceleration sensors) on each body part of the subject, acquire body composition information of each body part of the subject (only fat free mass of each body part) and determine an activity-induced energy expenditure by use of a formula (5): $AEE = (\alpha 1_1 + \beta 1_1 \times X \times W + \gamma 1_1 \times FFM_1 + \epsilon 1_1 \times A + \zeta 1_1 \times S) + (\alpha 1_2 + \beta 1_2 \times X \times W + \gamma 1_2 \times FFM_2 + \epsilon 1_2 \times A + \zeta 1_2 \times S) + \ldots + (\alpha 1_n + \beta 1_n \times X \times W + \gamma 1_n \times FFM_n + \epsilon 1_n \times A + \zeta 1_n \times S)$ wherein X represents acceleration, W represents a body weight, A represents age, S represents sex, $FFM_1$, $FFM_2$, ... $FFM_n$ (n represents the number of body parts) represent fat free masses of body parts, $\alpha 1_1, \alpha 1_2, \ldots \alpha 1_n$, $\beta 1_1, \beta 1_2, \ldots \beta 1_n, \gamma 1_1, \gamma 1_2, \ldots \delta 1_n, \epsilon 1_1, \epsilon 1_2, \ldots \epsilon 1_n, \zeta 1_1, \zeta 1_2, \ldots \zeta 1_n$ (n represents the number of body parts) represent constants and AEE represents an activity-induced energy expenditure. For example, as shown in FIG. 7, the instrument may place the detection section (five acceleration sensors 13a) on body parts (for example, trunk, right upper extremity, left upper extremity, right lower extremity, left lower extremity) of the subject 21, acquire body composition information of the body parts of the subject (fat free mass $FFM_1$ of the trunk, fat free mass $FFM_2$ of the right upper extremity, fat free mass $FFM_3$ of the left upper extremity, fat free mass $FFM_4$ of the right lower extremity, fat free mass $FFM_5$ of the left lower extremity) and determine an activity-induced energy expenditure by substituting the acquired information into a formula: $AEE=(\alpha_1+\beta_1 \times X \times W+\gamma_1 \times FFM_1+\epsilon_1 \times A+\zeta_1 \times S)+(\alpha_2+\beta_2 \times X \times W+\gamma_2 \times FFM_2+\epsilon_2 \times A+\zeta_2 \times S)+(\alpha_3+\beta_3 \times X \times W+\gamma_3 \times FFM_3+\epsilon_3 \times A+\zeta_3 \times S)+(\alpha_4+\beta_4 \times X \times W+\gamma_4 \times FFM_4+\epsilon_4 \times A+\zeta_4 \times S)+(\alpha_5+\beta_5 \times X \times W+\gamma_5 \times FFM_5+\epsilon_5 \times A+\zeta_5 \times S)$.

Thus, an activity-induced energy expenditure can be determined more securely and with ease and higher accuracy by taking into consideration the body activity information and body composition information of each body part of a subject.

What is claimed is:

1. An activity-induced energy expenditure estimating instrument comprising:
   body activity information measuring means,
   body specifying information acquiring means,
   body composition information acquiring means, and
   activity-induced energy expenditure computing means,
   wherein
   the body activity information measuring means measures body activity information,
   the body specifying information acquiring means acquires body specifying information,
   the body composition information acquiring means acquires body composition information, and
   the activity-induced energy expenditure computing means stores correlation data representing correlations between the body activity information, body specifying information, body composition information, and an activity-induced energy expenditure, and calculates an activity-induced energy expenditure corresponding to the body activity information measured by the body activity information measuring means, the body specifying information acquired by the body specifying information acquiring means and the body composition information acquired by the body composition information acquiring means, by use of the stored correlation data;
   wherein the body activity information is acceleration, the body specifying information is a body weight, age and sex, and the body composition information is at least one selected from the group consisting of a fat free mass, a muscle amount, a fat mass, total body water and a body cell mass; and
   wherein the correlation data is represented by a formula: $AEE=a_1+b_1 \times X \times W+c_1 \times FFM+d_1 \times A+f_1 \times S$ wherein X represents acceleration, W represents a body weight, A represents age, S represents sex, FFM represents a fat free mass, $a_1, b_1, c_1, d_1$ and $f_1$ represent constants, and AEE represents an activity-induced energy expenditure.

2. An activity-induced energy expenditure estimating instrument comprising:
   body activity information measuring means,
   body specifying information acquiring means,
   body composition information acquiring means, and
   activity-induced energy expenditure computing means,
   wherein
   the body activity information measuring means, measures body activity information,
   the body specifying information acquiring means acquires body specifying information,
   the body composition information acquiring means acquires body composition information, and
   the activity-induced energy expenditure computing means stores correlation data representing correlations between the body activity information, body specifying information, body composition information, and an activity-induced energy expenditure, and calculates an activity-induced energy expenditure corresponding to the body activity information measured by the body activity information measuring means, the body specifying information acquired by the body specifying information acquiring means and the body composition information acquired by the body composition information acquiring means, by use of the stored correlation data;
   wherein the body activity information is acceleration, the body specifying information is a body weight, age and sex, and the body composition information is at least one selected from the group consisting of a fat free mass, a muscle amount, a fat mass, total body water and a body cell mass; and
   wherein the correlation data is represented by a formula: $AEE=a_2+b_2 \times X \times W+c_2 \times FFM+d_2 \times FM+e_2 \times A+f_2 \times S$
   wherein X represents acceleration, W represents a body weight, A represents age, S represents sex, FFM represents a fat free mass, FM represents a fat mass, $a_2, b_2, c_2, d_2, e_2$ and $f_2$ represent constants, and AEE represents an activity-induced energy expenditure.

3. An activity-induced energy expenditure estimating instrument comprising:
   body activity information measuring means,
   body specifying information acquiring means,
   body composition information acquiring means, and
   activity-induced energy expenditure computing means,
   wherein
   the body activity information measuring means measures body activity information,
   the body specifying information acquiring means acquires body specifying information,
   the body composition information acquiring means acquires body composition information, and
   the activity-induced energy expenditure computing means stores correlation data representing correlations between the body activity information, body specifying information, body composition information, and an activity-induced energy expenditure, and calculates an activity-induced energy expenditure corresponding to the body activity information measured by the body activity information measuring means, the body specifying information acquired by the body specifying information acquiring means and the body composition information acquired by the body composition information acquiring means, by use of the stored correlation data;
   wherein the body activity information is acceleration, the body specifying information includes a body weight, age, sex and a body height, and the body composition information includes at least one of a fat free mass, a muscle amount, a fat mass, total body water and a body cell mass; and wherein the correlation data is represented by a formula: $AEE = a_3 + b_3 \times X \times W + c_3 \times FFM/H^2 + d_3 \times A + f_3 \times S$ wherein X represents acceleration, W represents a body weight, A represents age, S represents sex, H represents a body height, FFM represents a fat free mass, $a_3$, $b_3$, $c_3$, $d_3$ and $f_3$ represent constants, and AEE represents an activity-induced energy expenditure.

4. An activity-induced energy expenditure estimating instrument comprising:
body activity information measuring means,
body specifying information acquiring means,
body composition information acquiring means, and
activity-induced energy expenditure computing means,
wherein
the body activity information measuring means measures body activity information,
the body specifying information acquiring means acquires body specifying information,
the body composition information acquiring means acquires body composition information, and
the activity-induced energy expenditure computing means stores correlation data representing correlations between the body activity information, body specifying information, body composition information, and an activity-induced energy expenditure, and calculates an activity-induced energy expenditure corresponding to the body activity information measured by the body activity information measuring means, the body specifying information acquired by the body specifying information acquiring means and the body composition information acquired by the body composition information acquiring means, by use of the stored correlation data;
wherein the body activity information is acceleration, the body specifying information includes a body weight, age, sex and a body height, and the body composition information includes at least one of a fat free mass, a muscle amount, a fat mass, total body water and a body cell mass; and
wherein the correlation data is represented by a formula: $AEE = a_4 + b_4 \times X \times W + c_4 \times FFM/H^2 + d_4 \times FM + e_4 \times A + f_4 \times S$ wherein X represents acceleration, W represents a body weight, A represents age, S represents sex, H represents a body height, FFM represents a fat free mass, FM represents a fat mass, $a_4$, $b_4$, $c_4$, $d_4$, $e_4$ and $f_4$ represent constants, and AEE represents an activity-induced energy expenditure.

5. An activity-induced energy expenditure estimating instrument comprising:
body activity information measuring means,
body specifying information acquiring means,
body composition information acquiring means, and
activity-induced energy expenditure computing means,
wherein
the body activity information measuring means measures body activity information,
the body specifying information acquiring means acquires body specifying information,
the body composition information acquiring means acquires body composition information, and
the activity-induced energy expenditure computing means stores correlation data representing correlations between the body activity information, body specifying information, body composition information, and an activity-induced energy expenditure, and calculates an activity-induced energy expenditure corresponding to the body activity information measured by the body activity information measuring means, the body specifying information acquired by the body specifying information acquiring means and the body composition information acquired by the body composition information acquiring means, by use of the stored correlation data;
wherein the body composition information acquiring means acquires the body composition information from each body part, and the activity-induced energy expenditure computing means stores correlation data representing correlations between the body activity information, body specifying information and body composition information of each body part and an activity-induced energy expenditure, and calculates an activity-induced energy expenditure corresponding to the body activity information measured by the body activity information measuring means, the body specifying information acquired by the body specifying information acquiring means and the body composition information of each body part which has been acquired by the body composition information acquiring means;
wherein the body activity information is acceleration, the body specifying information is a body weight, age and sex, and the body composition information of each body part is at least one selected from the group consisting of a fat free mass of each body part, a muscle amount of each body part, a fat mass of each body part, total body water of each body part and a body cell mass of each body part; and
wherein the correlation data is represented by a formula: $AEE = (\alpha 1_1 + \beta 1_1 \times X \times W + \gamma 1_1 \times FFM_1 + \epsilon 1_1 \times A + \zeta 1_1 \times S) + (\alpha 1_2 + \beta 1_2 \times X \times W + \gamma 1_2 \times FFM_2 + \epsilon 1_2 \times A + \zeta 1_2 \times S) + \ldots + (\alpha 1_n + \beta 1_n \times X \times W + \gamma 1_n \times FFM_n + \epsilon 1_n \times A + \zeta 1_n \times S)$ wherein X represents acceleration, W represents a body weight, A represents age, S represents sex, $FFM_1$, $FFM_2$, $\ldots$ $FFM_n$ (n represents the number of body parts) represent fat free masses of body parts, $\alpha 1_1$, $\alpha 1_2$, $\ldots$ $\alpha 1_n$, $\beta 1_1$, $\beta 1_2$, $\ldots$ $\beta 1_n$, $\gamma 1_1$, $\gamma 1_2$, $\ldots$ $\gamma 1_n$, $\epsilon 1_1$, $\epsilon 1_2$, $\ldots$ $\epsilon 1_n$, $\zeta 1_1$, $\zeta 1_2$, $\ldots$ $\zeta 1_n$ (n represents the number of body parts) represent constants, and AEE represents an activity-induced energy expenditure.

6. An activity-induced energy expenditure estimating instrument comprising:
body activity information measuring means,
body specifying information acquiring means,
body composition information acquiring means, and
activity-induced energy expenditure computing means,
wherein
the body activity information measuring means measures body activity information,
the body specifying information acquiring means acquires body specifying information,
the body composition information acquiring means acquires body composition information, and
the activity-induced energy expenditure computing means stores correlation data representing correlations between the body activity information, body specifying information, body composition information, and an activity-induced energy expenditure, and calculates an activity-induced energy expenditure corresponding to the body activity information measured by the body activity information measuring means, the body specifying information acquired by the body specifying information acquiring means and the body composition information acquired by the body composition information acquiring means, by use of the stored correlation data;

wherein the body composition information acquiring means acquires the body composition information from each body part, and the activity-induced energy expenditure computing means stores correlation data representing correlations between the body activity information, body specifying information and body composition information of each body part and an activity-induced energy expenditure, and calculates an activity-induced energy expenditure corresponding to the body activity information measured by the body activity information measuring means, the body specifying information acquired by the body specifying information acquiring means and the body composition information of each body part which has been acquired by the body composition information acquiring means;

wherein the body activity information is acceleration, the body specifying information is a body weight, age and sex, and the body composition information of each body part is at least one selected from the group consisting of a fat free mass of each body part, a muscle amount of each body part, a fat mass of each body part, total body water of each body part and a body cell mass of each body part; and wherein the correlation data is represented by a formula:
$AEE=(\alpha 2_1+\beta 2_1 \times X \times W+\gamma 2_1 \times FFM_1+\delta 2_1 \times FM_1+\epsilon 2_1 \times A+\zeta 2_1 \times S)+(\alpha 2_2+\beta 2_2 \times X \times W+\gamma 2_2 \times FFM_2+\delta 2_2 \times FM_2+\epsilon 2_2 \times A+\zeta 2_2 \times S)+ \ldots +(\alpha 2_n+\beta 2_n \times X \times W+\gamma 2_n \times FFM_n+\delta 2_n \times FM_n+\epsilon 2_n \times A+\zeta 2_n \times S)$ wherein X represents acceleration, W represents a body weight, A represents age, S represents sex, $FFM_1, FFM_2, \ldots FFM_n$ (n represents the number of body parts) represent fat free masses of body parts, $FM_1, FM_2, \ldots FM_n$ (n represents the number of body parts) represent fat masses of body parts, $\alpha 2_1, \alpha 2_2, \ldots \alpha 2_n, \beta 2_1, \beta 2_2, \ldots \beta 2_n, \gamma 2_1, \gamma 2_2, \ldots \gamma 2_n, \delta 2_1, \delta 2_2, \ldots \delta 2_n, \epsilon 2_1, \epsilon 2_2, \ldots \epsilon 2_n, \zeta 2_1, \zeta 2_2, \ldots \zeta 2_n$ (n represents the number of body parts) represent constants, and AEE represents an activity-induced energy expenditure.

7. The instrument of any one of claims 1, 2, 3, 4, 5, and 6, further comprising:

basal energy expenditure acquiring means, diet-induced energy expenditure acquiring means, and total energy expenditure computing means, wherein the basal energy expenditure acquiring means acquires a basal metabolic rate or a rest metabolic rate, the diet-induced energy expenditure acquiring means acquires a diet-induced energy expenditure, and the total energy expenditure computing means calculates a total energy expenditure by totaling the activity-induced energy expenditure acquired by the activity-induced energy expenditure computing means, the basal metabolic expenditure acquired by the basal energy expenditure acquiring means and the diet-induced energy expenditure acquired by the diet-induced energy expenditure acquiring means.

* * * * *